United States Patent
Kwon et al.

(10) Patent No.: US 8,686,151 B2
(45) Date of Patent: Apr. 1, 2014

(54) MONTELUKAST 4-HALOBENZYLAMINE SALT AND METHOD FOR PREPARING MONTELUKAST SODIUM SALT BY USING THE SAME

(71) Applicant: Dong Kook Pharm. Co., Ltd., Seoul (KR)

(72) Inventors: Hyuk Chul Kwon, Suwon (KR); Man Dong Rho, Seoul (KR); Kyung Hoi Cha, Yongin (KR)

(73) Assignee: Dong Kook Pharm. Co., Ltd., Seoul (KR)

( * ) Notice: Subject to any disclaimer, the term of this patent is extended or adjusted under 35 U.S.C. 154(b) by 0 days.

(21) Appl. No.: 13/730,168

(22) Filed: Dec. 28, 2012

(65) Prior Publication Data

US 2013/0184464 A1  Jul. 18, 2013

Related U.S. Application Data

(63) Continuation of application No. PCT/KR2011/005566, filed on Jul. 28, 2011.

(30) Foreign Application Priority Data

Jul. 30, 2010  (KR) .................. 10-2010-0074005

(51) Int. Cl.
  *C07D 215/14*  (2006.01)
(52) U.S. Cl.
  USPC ........................................ 546/174
(58) Field of Classification Search
  None
  See application file for complete search history.

(56) References Cited

U.S. PATENT DOCUMENTS

| 8,115,004 | B2 * | 2/2012 | Reddy et al. | 546/174 |
| 8,188,285 | B2 * | 5/2012 | Gasanz Guillen et al. | 546/174 |
| 2009/0281323 | A1 * | 11/2009 | Chawla et al. | 546/174 |

* cited by examiner

Primary Examiner — Janet L Andres
Assistant Examiner — Timothy R Rozof
(74) Attorney, Agent, or Firm — Edwards Wildman Palmer LLP

(57) ABSTRACT

Disclosed are a novel montelukast 4-halobenzylamine salt, and a method for preparing a montelukast sodium salt by using the same. In the disclosed method, a montelukast 4-halobenzylamine salt represented by Formula 2 or a montelukast sodium salt represented by Formula 1 is prepared by obtaining a compound represented by Formula 3 from a compound represented by Formula 5, in the same reactor, without an additional obtaining process.

[Formula 1]

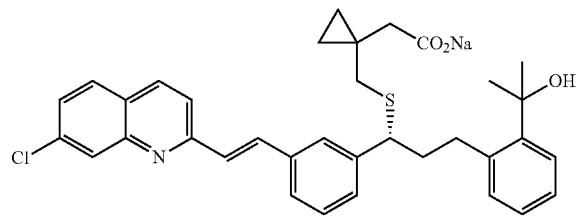

[Formula 2]

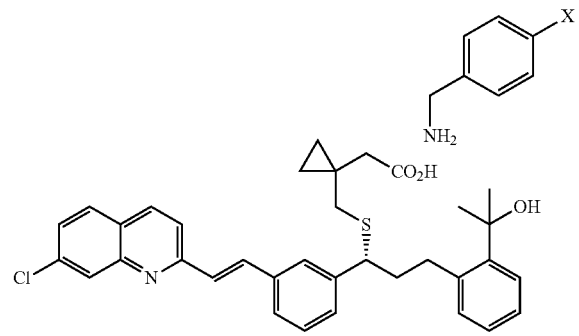

In Formula 2, X represents F, Cl, Br or I.

14 Claims, 6 Drawing Sheets

MONTELUKAST 4-HALOBENZYLAMINE SALT AND METHOD FOR PREPARING MONTELUKAST SODIUM SALT BY USING THE SAME

CROSS REFERENCE TO RELATED APPLICATION

This application is a continuation of International Application No. PCT/KR2011/005566 filed on Jul. 28, 2011, which claims priority to Korean Application No. 10-2010-0074005 filed on Jul. 30, 2010, which applications are incorporated herein by reference.

BACKGROUND OF THE INVENTION

1. Field of the Invention

The present invention relates to a novel montelukast amine salt, and a method for preparing a montelukast sodium salt by using the same.

2. Description of the Prior Art

A montelukast sodium salt, as represented by Formula 1 below, is a leukotriene receptor antagonist. Leukotriene is related to contraction and inflammation of airway muscles, and fluid accumulation within the lung, and is currently useful as a therapeutic agent for respiratory system diseases such as asthma and allergic rhinitis. Montelukast sodium salt was first developed by Merck & Co., Inc. and is commercially available as Singulair®, which is a moisture-absorbing and optically active white (or pale white) powder having the structural formula below, and is soluble in methanol, ethanol or water, and insoluble in acetonitrile.

[Formula 1]

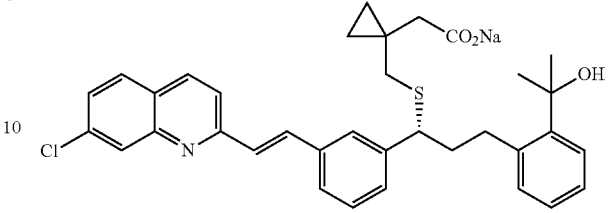

Since a montelukast sodium salt contains an asymmetric carbon atom, it is very difficult to secure chiral purity of montelukast and obtain a highly pure montelukast sodium salt.

In synthesis of a montelukast sodium salt, a low yield and a difficult purification process have been always problematic due to the complicated purification method.

First, Korean Registered Patent No. 227716, and EU Patent No. 480717 disclosed a method for synthesizing montelukast acid, represented by Reaction Scheme 1 below. However, the preparation method requires not only an additional process for introducing and removing a tetrahydropyranyl protecting group, but also a purification process through chromatography. Thus, it is difficult to employ the method in mass production. Furthermore, there is a problem in that the method is not suitable for mass production due to a low yield.

[Reaction Scheme 1]

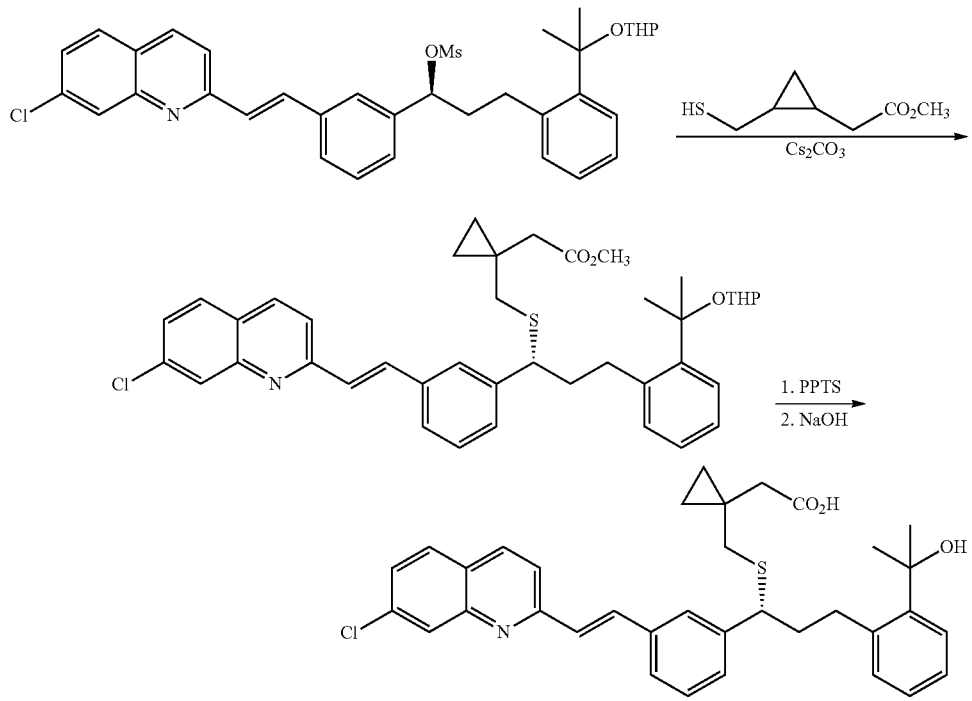

Korean Registered Patent No. 899585 disclosed a montelukast isopropylamine salt prepared by Reaction Scheme 2 below, and a method for preparing a montelukast sodium salt by using the same salt. However, there are disadvantages such as a low yield of isopropylamine salt and a low total yield of sodium salt.

[Reaction Scheme 2]

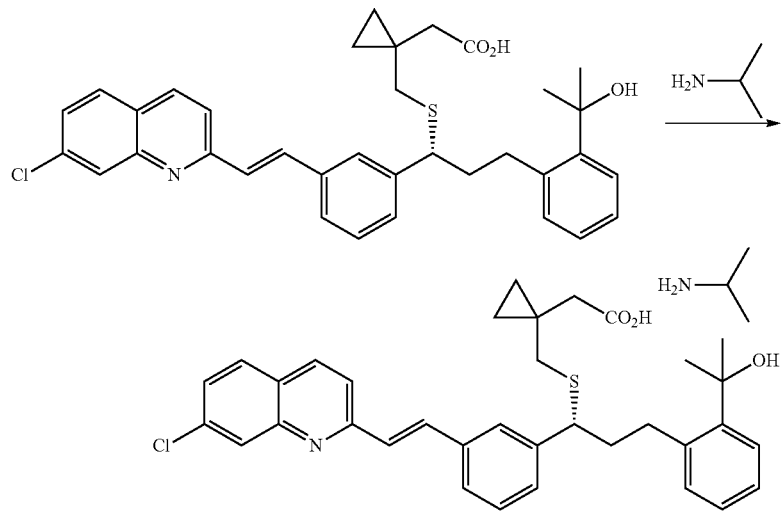

International Publication WO 2007/004237 disclosed a method for preparing a montelukast sodium salt by using α-methyl benzylamine. However, in the method, the purity and yield are not described. Also, Korean Registered Patent No. 920314 disclosed a method for preparing a montelukast sodium salt by using a montelukast benzylamine salt. However, the method has a problem in that the total yield of the benzylamine salt is significantly low (about 50%), and also the yield of the sodium salt is low.

Accordingly, in order to solve problems (such as low purity, and low yield) in a method for preparing a montelukast sodium salt by using conventionally known salts of montelukast, the inventors of the present invention have struggled to research a novel salt of montelukast. As a result, they have completed the present invention by developing a novel montelukast 4-halobenzylamine salt. Through the developed novel montelukast amine salt, it is possible to prepare a montelukast sodium salt with a high purity and a high yield, compared to conventionally disclosed methods. Thus, it is possible to very economically and efficiently mass-produce the montelukast sodium salt.

SUMMARY OF THE INVENTION

Accordingly, the present invention has been made to solve the above-mentioned problems occurring in the prior art, and an object of the present invention is to provide a novel montelukast 4-halobenzylamine salt, and a preparation method thereof.

Another object of the present invention is to provide a method for preparing a montelukast sodium salt by using a novel montelukast 4-halobenzylamine salt.

In order to accomplish this object, there is provided a montelukast 4-halobenzylamine salt represented by Formula 2 below:

[Formula 2]

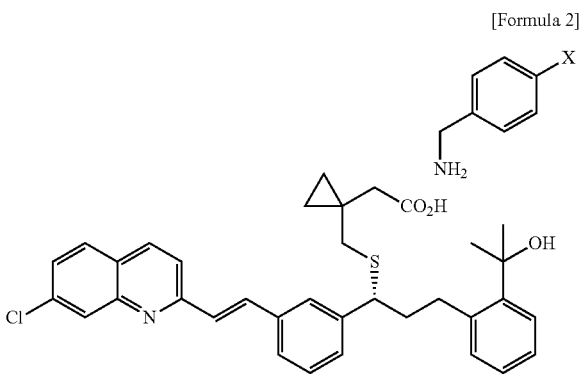

wherein in Formula 2, X represents F, Cl, Br or I.

In accordance with another aspect of the present invention, there is provided a method for preparing a montelukast 4-halobenzylamine salt represented by Formula 2 below, wherein a compound represented by Formula 3 is reacted with 4-halobenzylamine,

[Formula 2]

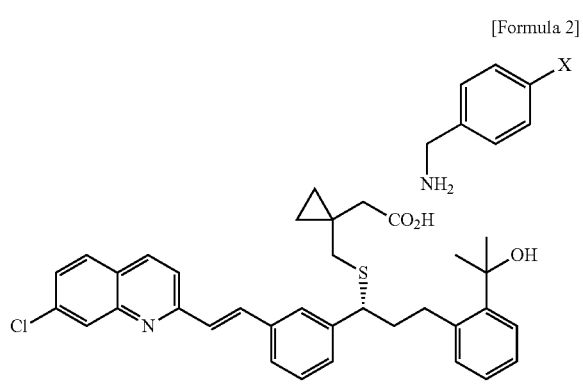

-continued

[Formula 3]

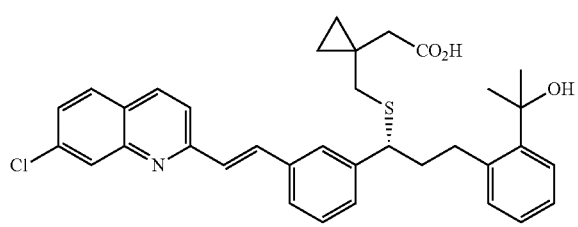

wherein in Formula 2,
X represents F, Cl, Br or I.

In accordance with a further aspect of the present invention, there is provided a method for preparing a montelukast 4-halobenzylamine salt represented by Formula 2, the method including the steps of:

a) obtaining a compound represented by Formula 3 below by reacting a compound represented by Formula 5 below with methanesulfonyl chloride, then with a compound represented by Formula 4, followed by base treatment; and b) obtaining a compound represented by Formula 2 by reacting the obtained compound represented by Formula 3 with 4-halobenzylamine,

[Formula 2]
[Formula 3]
[Formula 4]
[Formula 5]

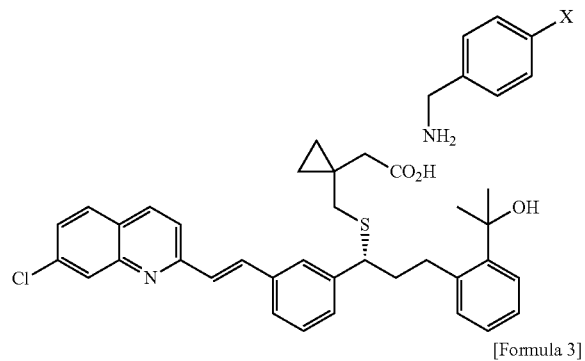

wherein in Formula 2, X represents F, Cl, Br or I.

Herein, in the base treatment, a base conventionally used in the art may be used. For example, sodium hydroxide may be used.

In the inventive method for preparing a montelukast 4-halobenzylamine salt, step a) is preferably to obtain a compound represented by Formula 3 by reacting a compound represented by Formula 5 with methanesulfonyl chloride, then with a compound represented by Formula 4, followed by base treatment, without an additional obtaining process.

In the inventive method for preparing the montelukast 4-halobenzylamine salt, the reaction with the compound represented by Formula 4 in step a) is preferably carried out in at least one base selected from the group consisting of cesium carbonate, lithium hydroxide, sodium hydroxide, potassium hydroxide, potassium carbonate, and sodium carbonate, and preferably in cesium carbonate.

In the inventive method for preparing the montelukast 4-halobenzylamine salt, the step of reacting the compound represented by Formula 3 with the 4-halobenzylamine is preferably carried out in at least one solvent selected from the group consisting of ethanol, isopropyl alcohol, acetone, acetonitrile, ethyl acetate, tetrahydrofuran, methylene chloride, chloroform, toluene, xylene, hexane, cyclohexane and heptane.

In accordance with a still further aspect of the present invention, there is provided a method for preparing a montelukast sodium salt represented by Formula 1 below, the method including the steps of:

1) obtaining a compound represented by Formula 2 below by reacting a compound represented by Formula 3 below with 4 halobenzylamine; and 2) treating the obtained compound represented by Formula 2 with acid, and attaching sodium thereto,

[Formula 1]

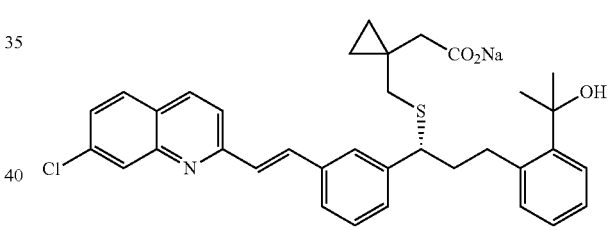

[Formula 2]

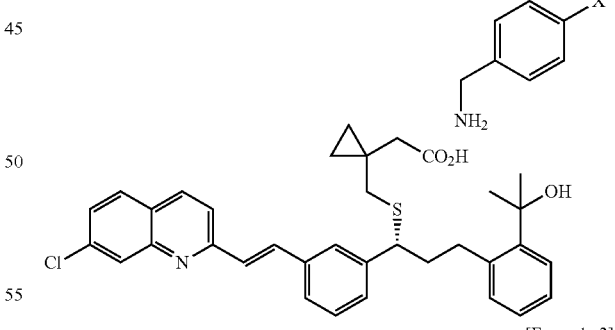

[Formula 3]

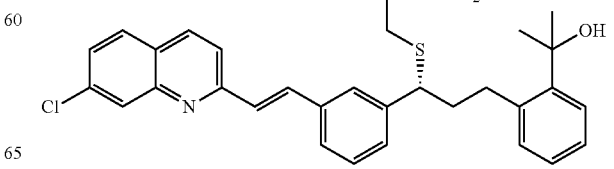

wherein in Formula 2,

X represents F, Cl, Br or I.

In accordance with a yet still further aspect of the present invention, there is provided a method for preparing a montelukast sodium salt represented by Formula 1 below, the method including the steps of:

a) obtaining a compound represented by Formula 3 below by reacting a compound represented by Formula 5 below with methanesulfonyl chloride, then with a compound represented by Formula 4 below, followed by base treatment;

b) obtaining a compound represented by Formula 2 below by reacting the obtained compound represented by Formula 3 with 4-halobenzylamine, and c) treating the obtained compound represented by Formula 2 with acid, and attaching sodium thereto,

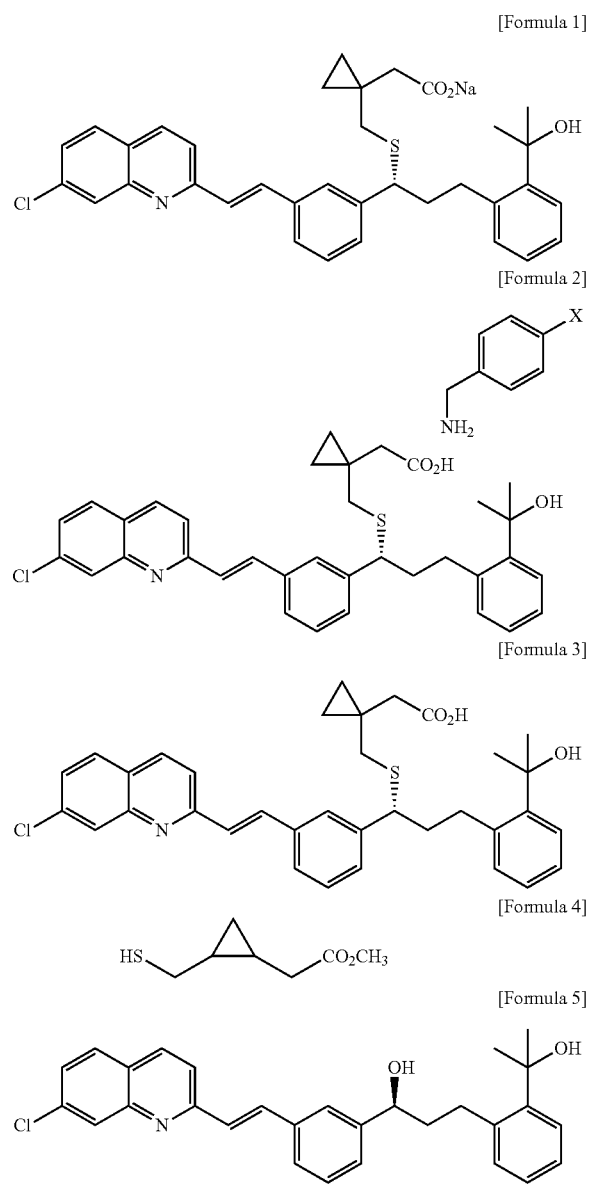

[Formula 1]

[Formula 2]

[Formula 3]

[Formula 4]

[Formula 5]

wherein in Formula 2, X represents F, Cl, Br or I.

Herein, in the base treatment, a base conventionally used in the art may be used. For example, sodium hydroxide may be used.

In the inventive method for preparing a montelukast sodium salt, step a) is preferably to obtain a compound represented by Formula 3 by reacting a compound represented by Formula 5 with methanesulfonyl chloride, then with a compound represented by Formula 4, followed by base treatment, without an additional obtaining process.

In the inventive method for preparing the montelukast sodium salt, the reaction with the compound represented by Formula 4 in step a) is preferably carried out in at least one base selected from the group consisting of cesium carbonate, lithium hydroxide, sodium hydroxide, potassium hydroxide, potassium carbonate, and sodium carbonate, and preferably in cesium carbonate.

In the inventive method for preparing the montelukast sodium salt, the step of obtaining the compound represented by Formula 2 by reacting the compound represented by Formula 3 with the 4-halobenzylamine is preferably carried out in at least one solvent selected from the group consisting of ethanol, isopropyl alcohol, acetone, acetonitrile, ethyl acetate, tetrahydrofuran, methylene chloride, chloroform, toluene, xylene, hexane, cyclohexane and heptane.

In the inventive method for preparing the montelukast sodium salt, in the step of attaching sodium, at least one selected from the group consisting of sodium hydroxide, sodium methoxide, and tert-sodium butoxide is preferably added.

According to the present invention, a novel montelukast 4-halobenzylamine salt can be synthesized with a high yield of 88% or more, and a high purity of 98.3% or more through 4-halobenzylamine and montelukast acid represented by Formula 3. Also, through the novel montelukast 4-halobenzylamine salt, a montelukast sodium salt can be mass-produced with a high yield of 98% or more and a high purity of 99.6% or more. Furthermore, in the inventive method for preparing the montelukast sodium salt, a continuous process is used so as to simplify the production process, reduce production time, and decrease the amount of solvent. This provides an efficient and economical mass-production method.

BRIEF DESCRIPTION OF THE DRAWINGS

The above and other objects, features and advantages of the present invention will be more apparent from the following detailed description taken in conjunction with the accompanying drawings, in which.

Figure 1:
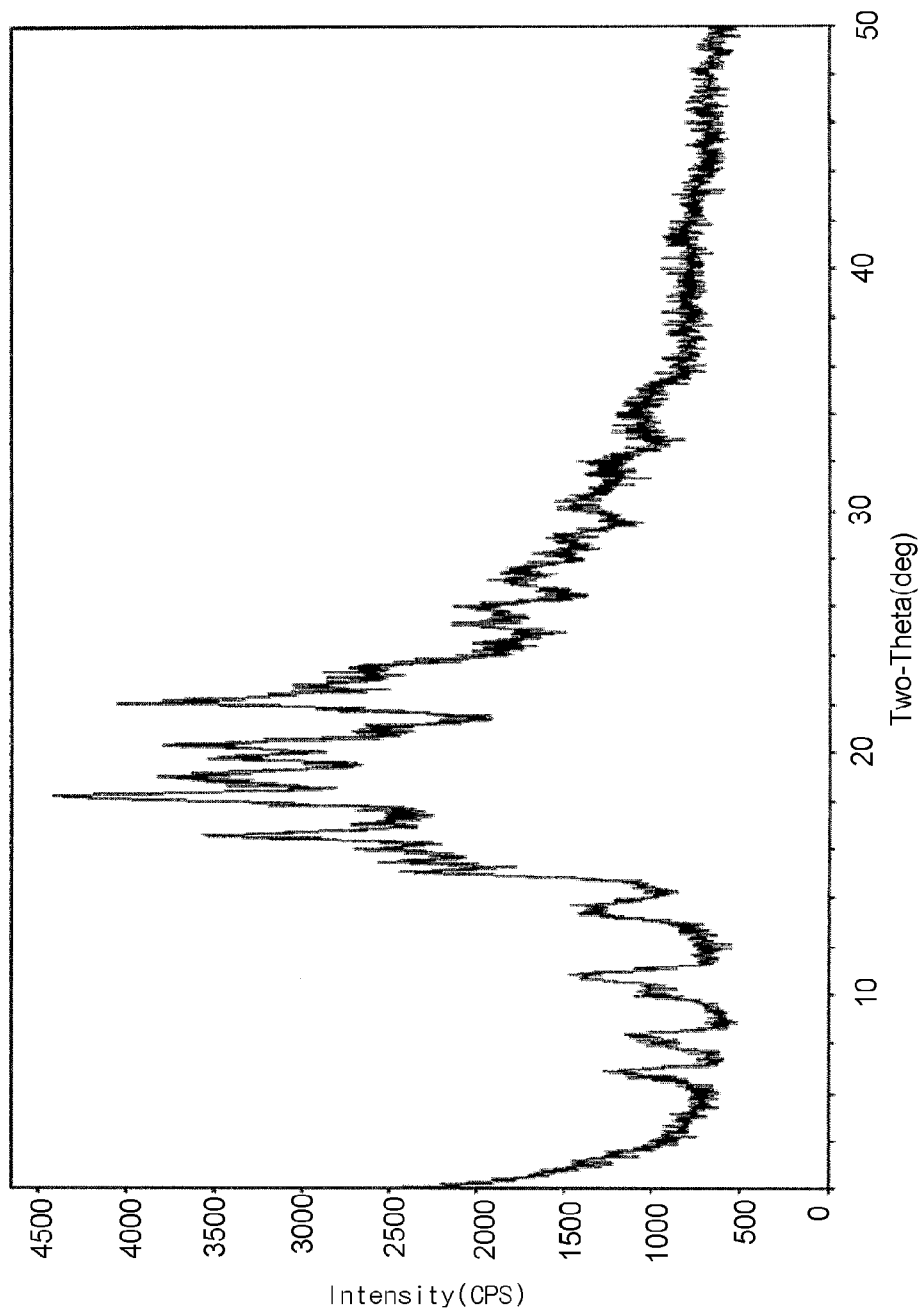
FIG. 1 shows an X-ray powder diffraction diagram of a montelukast 4-chlorobenzylamine salt prepared from Example 3.
Figure 2:
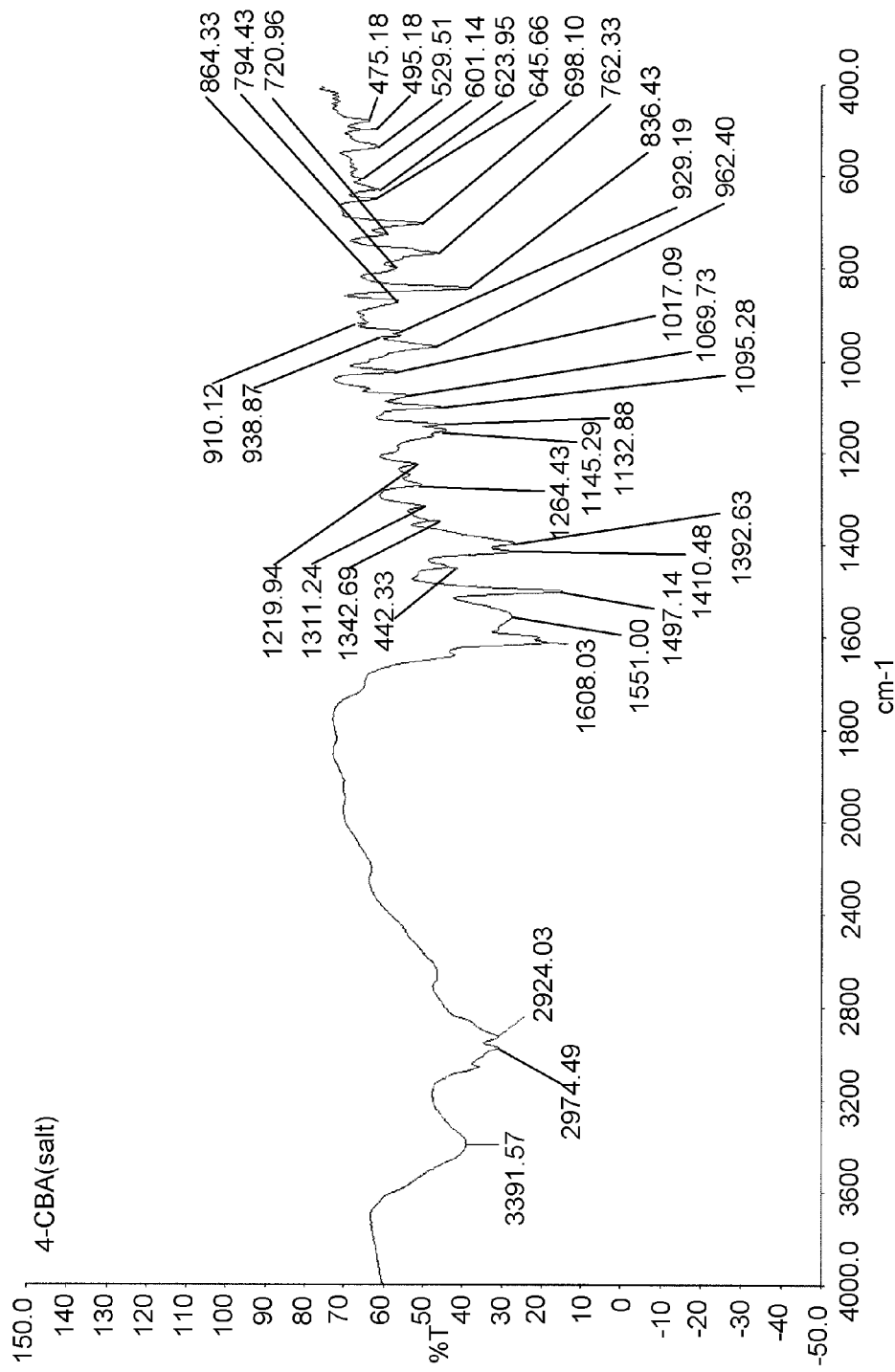
FIG. 2 shows an FT-IR spectrum of a montelukast 4-chlorobenzylamine salt prepared from Example 3.
Figure 3:
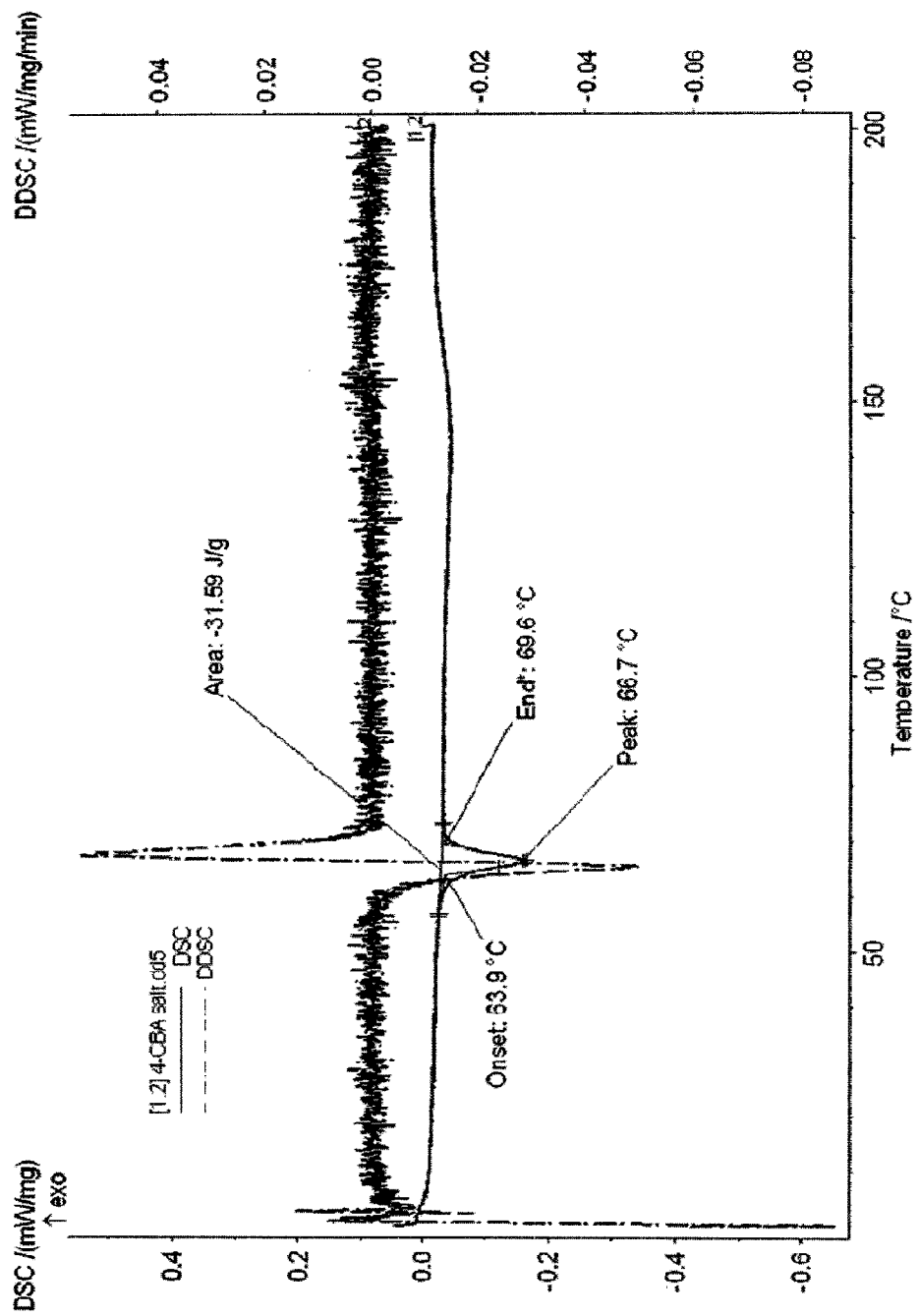
FIG. 3 shows a DSC diagram of a montelukast 4-bromobenzylamine salt prepared from Example 3.
Figure 4:
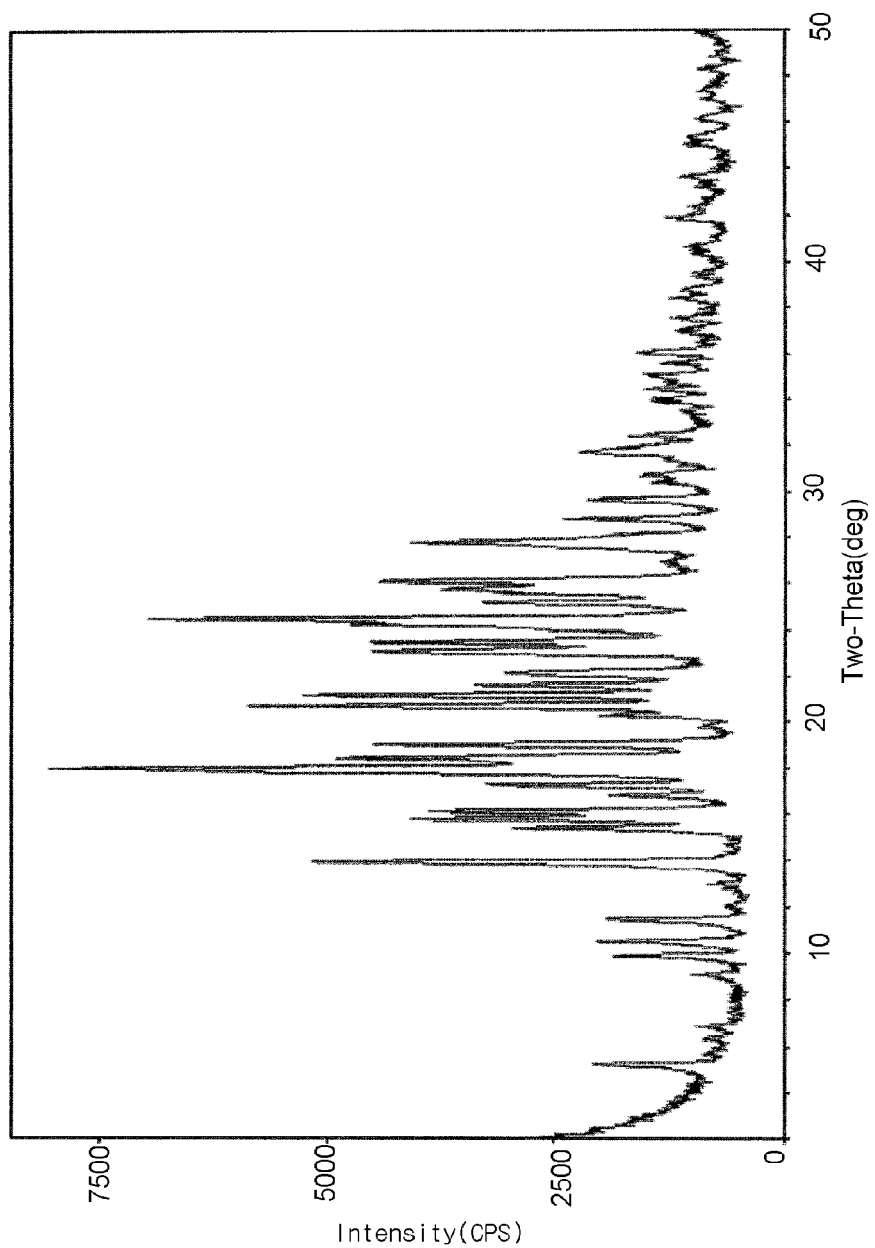
FIG. 4 shows an X-ray powder diffraction diagram of a montelukast 4-bromobenzylamine salt prepared from Example 4.
Figure 5:
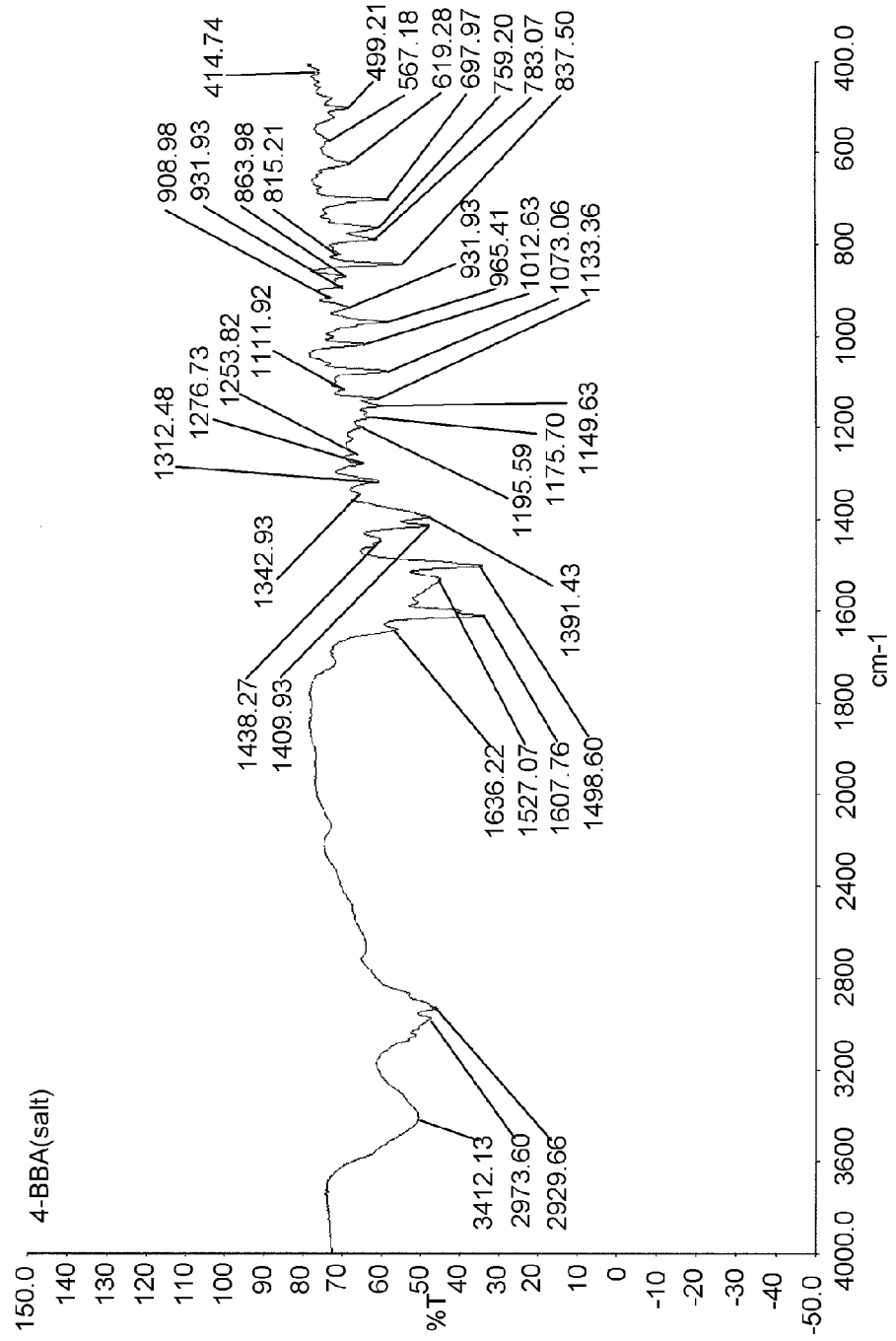
FIG. 5 shows an FT-IR spectrum of a montelukast 4-bromobenzylamine salt prepared from Example 4.
Figure 6:
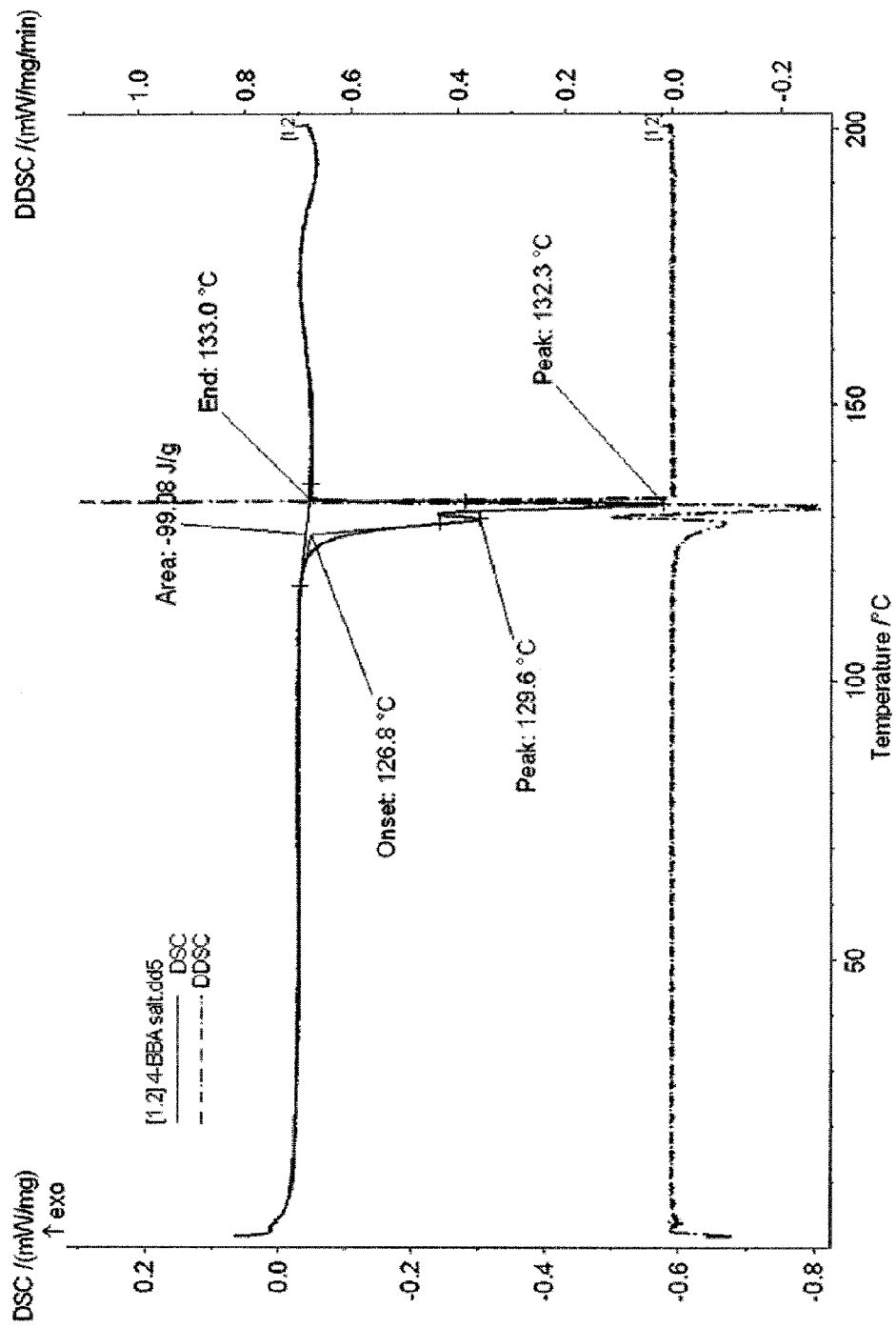
FIG. 6 shows a DSC diagram of a montelukast 4-bromobenzylamine salt prepared from Example 4.

DETAILED DESCRIPTION OF
REPRESENTATIVE EMBODIMENTS

According to the present invention, a montelukast acid may be synthesized through Reaction Scheme 3, and then finally, a montelukast sodium salt may be synthesized in accordance with the method of Reaction Scheme 5.

[Reaction Shceme 3]

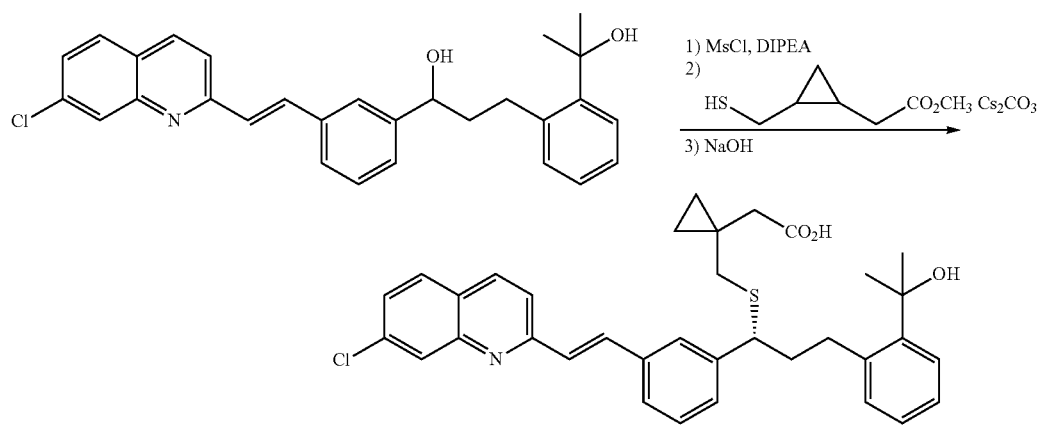

As shown in Reaction Scheme 3, mesylation is carried out by using a diol derivative as a starting material, and then a coupling reaction is carried out without a further separation. After the completion of the reaction, the steps from introduction of sodium hydroxide to hydrolysis are carried out as one process, minimizing a loss caused by separation of a mesylate compound. This improves the yield, simplifies the process, and reduces the amount of solvent. Through the method as described above, a montelukast acid represented by Compound 3 may be prepared with a purity of 91% or more, and a yield of 95% or more.

Through Reaction Scheme 4 below, a novel montelukast amine salt may be synthesized. Besides the halobenzylamine used in the present invention, various kinds of benzylamine derivatives and dicyclohexylamine were used to carry out comparative experiments.

In the synthesis of a montelukast sodium salt, in order to overcome problems (such as a low yield and a low purity) caused by a complicated purification method, as shown in Reaction Scheme 4,4-chlorobenzylamine or 4-bromobenzylamine is subjected to crystallization in a cosolvent, such as isopropyl alcohol/hexane, ethanol/hexane, ethyl acetate/hexane, so that a montelukast amine salt can be synthesized with a yield of 93%, and a purity of 99.5% or more.

The inventive crystalline montelukast amine salt was analyzed through powder X-ray diffraction and was subjected to a differential scanning calorimetric (DSC) analysis.

The montelukast amine salt obtained as described above may be subjected to freeze-drying or precipitation-crystallization in accordance with the method as described in Reaction Scheme 5 below so as to provide a montelukast sodium salt with a yield of 98%, a purity of 99.5%, and an optical purity of 99.9% ee or more.

[Reaction Shceme 4]

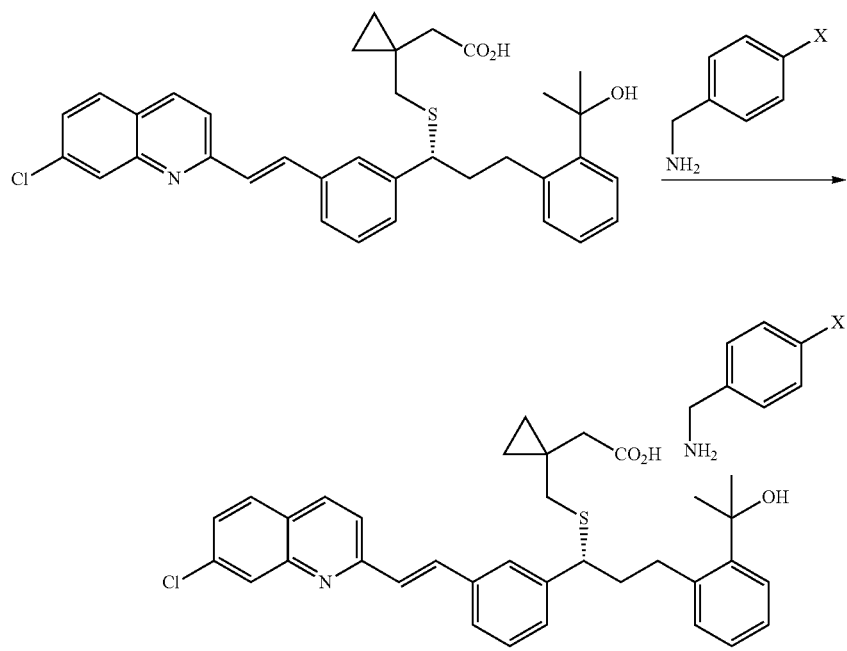

[Reaction Scheme 5]

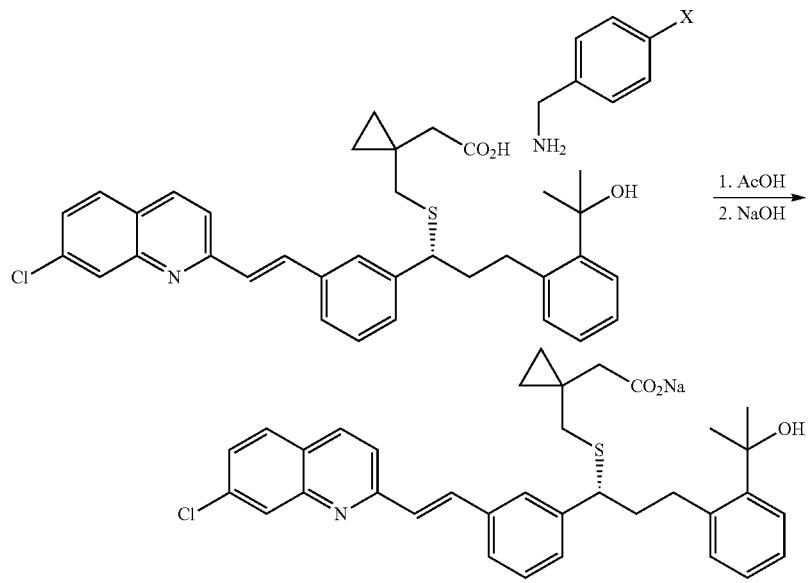

Hereinafter, the present invention will be described in more detail with reference to examples. However, the following examples are only for illustrative purposes and are not intended to limit the scope of the invention.

(X-ray powder diffraction data was obtained by using a D/max-2500V/PC (Rigaku) provided with an rpm meter and a solid state detector within an analysis range of 2°~50° (diffraction angle: 2θ) in accordance with a method known in the art.

DSC was measured by using a DSC 200 F3 (NETZSCH), at a heating rate of 1° C./min, within a temperature range of 25° C. to 200° C.)

EXAMPLE 1

Preparation of 1-(((1(R)-(3-(2-(7-chloro-2-quinolinyl)ethenyl)phenyl)-3-(2-(1-hydroxy-1-methylethyl)phenyl)propyl)thio)methyl)cyclopropane acetic acid (montelukast acid)

20 g of (1S)-1-(3-((E)-2-(7-chloroquinoline-2-yl)ethenyl)phenyl)-3-(2-(2-hydroxypropane-2-yl))propane-1-ol was dissolved in 40 ml of tetrahydrofuran and 40 ml of toluene. The resultant product was cooled at −15° C. and 3.55 mL of methanesulfonyl chloride was added thereto. At −15° C., 15.2 mL of diisopropylethylamine was dropped into it, and then stirring was carried out for 1 hour.

10.5 g of methyl 2-(2-(sulfanylmethyl)cyclopropyl)acetate was dissolved in 50 ml of dimethylformamide, and 42.7 g of cesium carbonate was added thereto. After stirring at room temperature, the resultant product was washed with 40 ml of dimethylformamide and dropped into a mesylate solution for 30 min. After the reaction was completed through stirring for 2 to 3 hours, 20 ml of distilled water was introduced. Then, 35 g of sodium hydroxide was added to the reaction product, it was heated up to 60° C., and stirred for 3 to 5 hours. When the reaction was completed, the resultant product was cooled to room temperature.

200 ml of methylene chloride was added to the reaction solution, and it was then washed with 200 ml of pure water twice so as to remove any excess of sodium hydroxide. 5.3 g of acetic acid dissolved in 200 ml of pure water was introduced to wash the resultant product. Then, the product was washed with 200 ml of salt water, and the organic layer was dehydrated with magnesium sulfate, filtered and vacuum-concentrated so as to provide 24.3 g of montelukast acid (yield: 95%, purity: 91.6%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm) 8.12(d, 1H), 8.05(d, 1H), 7.54~7.81(m, 4H), 7.09~7.48(m, 9H), 4.02(t, 1H), 3.14~3.24(m, 1H), 2.89~2.98(m, 1H), 2.70(dd, 2H), 2.16~2.33(m, 4H), 1.63(d, 6H), 0.47~0.55(m, 4H)

EXAMPLE 2

Preparation of 1-(((1(R)-(3-(2-(7-chloro-2-quinolinil)ethenyl)phenyl)-3-(2-(1-hydroxy-1-methylethyl)phenyl)propyl)thio)methyl)cyclopropane acetic acid 4-chloro benzylamine salt To 10 g of montelukast acid from Example 1, 200 ml of isopropyl alcohol was introduced, and the mixture was stirred. At room temperature, to the resultant product, 2.5 g of 4-chloro benzylamine was introduced, followed by stirring. When crystallized, the reaction mixture was heated up to 50° C. Then, the reaction mixture was stirred while 100 ml of normal hexane was dropped into it. The resultant product was stirred at 50° C. for 3 hours, gradually cooled to room temperature, further stirred for 3 hours, and filtered.

Through vacuum-drying at 50° C. for 12 hours, 10.8 g of montelukast 4-chlorobenzylamine salt was obtained (yield: 87%, purity: 98.5%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm): 8.10(d, 1H), 8.02(d, 1H), 7.72~7.61(m, 4H), 7.46~7.07(m, 13H), 4.01(t, 1H), 3.84

(s, 2H), 3.21~3.13(m, 1H), 2.94~2.84(m, 1H), 2.64(d, 1H), 2.49~2.14(m, 5H), 1.60(d, 6H), 0.55~0.40(m, 4H)

EXAMPLE 3

Preparation of 1-(((1(R)-(3-(2-(7-chloro-2-quinolinil)ethenyl)phenyl)-3-(2-(1-hydroxy-1-methylethyl)phenyl)propyl)thio)methyl)cyclopropane acetic acid 4-bromo benzylamine salt To 10 g of montelukast acid from Example 1, 200 ml of methanol was introduced, and the mixture was stirred. At room temperature, to the resultant product, 3.2 g of 4-bromo benzylamine was introduced, followed by stirring for 1 hour. Then, methanol was vacuum-concentrated, and 100 ml of isopropyl alcohol was introduced, followed by stirring. When crystallized, the reaction mixture was heated up to 50° C. Then, the reaction mixture was stirred while 100 ml of normal hexane was dropped into it. The resultant product was stirred at 50° C. for 3 hours, gradually cooled to room temperature, further stirred for 3 hours, and filtered.

Through vacuum-drying at 50° C. for 12 hours, 10.9 g of montelukast 4-bromo benzylamine salt was obtained (yield: 88%, purity: 98.3%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm): 8.13(d, 1H), 8.04(d, 1H), 7.79~7.61(m, 4H), 7.51~7.08(m, 13H), 4.01(t, 1H), 3.83 (s, 2H), 3.22~3.14(m, 1H), 2.98~2.91(m, 1H), 2.73(d, 1H), 2.62~2.16(m, 5H), 1.63(d, 6H), 0.58~0.46(m, 4H)

EXAMPLE 4

Preparation of 1-(((1(R)-(3-(2-(7-chloro-2-quinoliflethenyl)phenyl)-3-(2-(1-hydroxy-1-methylethyl)phenyl)propyl)thio)methyl)cyclopropane acetic acid 4-chlorobenzylamine salt To 10 g of montelukast amine salt obtained from Example 2, 100 ml of isopropyl alcohol was introduced. The mixture was heated up to 50° C., and stirred for 1 hour while 200 ml of normal hexane was dropped into it. The resultant product was stirred at 50° C. for 3 hours, gradually cooled to room temperature and then to 0° C., further stirred for 3 hours, and filtered.

Through vacuum-drying at 50° C. for 12 hours, 9.3 g of montelukast 4-chlorobenzylamine salt was obtained (yield: 93%, purity: 99.6%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

EXAMPLE 5

Preparation of sodium 1-(((1(R)-(3-(2-(7-chloro-2-quinolinil)ethenyl)phenyl)-3-(2-(1-hydroxy-1-methylethyl)phenyl)propyl)thio)methyl)cyclopropane acetate 10 g of montelukast amine salt obtained from Example 4 was dissolved in 100 ml of methylene chloride, and 10% acetic acid was dropped into it so as to adjust the pH to a range of 4 to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was dissolved in 20 ml of water and freeze-dried so as to provide 8.3 g of montelukast sodium salt (yield: 99%, purity: 99.6%, chiral purity: 99.9% ee, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm): 7.98(d, 1H), 7.94(d, 1H), 7.62~7.47(m, 4H), 7.40~6.96(m, 9H), 3.93(t, 1H), 3.19~3.33(m, 1H), 2.65~2.79(m, 1H), 2.48~2.35(m, 2H), 2.27~2.11(m, 4H), 1.55(d, 6H), 0.38~0.14(m, 4H)

EXAMPLE 6

Preparation of sodium 1-(((1(R)-(3-(2-(7-chloro-2-quinolinil)ethenyl)phenyl)-3-(2-(1-hydroxy-1-methylethyl)phenyl)propyl)thio)methyl)cyclopropane acetate 10 g of montelukast amine salt obtained from Example 3 was dissolved in 100 ml of methylene chloride, and 10% acetic acid was dropped into it so as to adjust the pH to a range of to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was crystallized using toluene and normal heptane so as to provide 8.2 g of montelukast sodium salt (yield: 98%, purity: 99.7%, chiral purity: 99.9% ee, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

COMPARATIVE EXAMPLE 1

Preparation of 1-(((1(R)-(3-(2-(7-chloro-2-quinoliflethenyl)phenyl)-3-(2-(1-hydroxy-1-methylethyl)phenyl)propyl)thio)methyl)cyclopropane acetic acid α-methylbenzylamine salt To 10 g of montelukast acid from Example 1, 60 ml of ethyl acetate was introduced. The mixture was stirred at 45° C. and cooled to 20 to 25° C. To the resultant product, 2 g of α-methylbenzylamine was introduced, followed by stirring for 1 hour. A seed was introduced, and stirring was carried out for 24 hours. Then, at 20 to 25° C., 120 ml of normal heptane was dropped into it for 1 hour, and stirring was further carried out for 24 hours.

The produced crystal was filtered, washed with normal heptane, and vacuum-dried at 50° C. for 12 hours so as to provide 9.2 g of montelukast amine salt (yield: 76%, purity: 96.7%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm) 8.10(d, 1H), 8.04(d, 1H), 7.61~7.73(m, 4H), 7.07~7.46(m, 14H), 4.15(q, 1H), 4.00(t, 1H), 3.14~3.19(m, 1H), 2.88~2.94(m, 1H), 2.62(d, 1H), 2.15~2.49(m, 5H), 1.60(d, 6H), 1.43(d, 3H), 0.40~0.55 (m, 4H)

COMPARATIVE EXAMPLE 2

Preparation of 1-(((1(R)-(3-(2-(7-chloro-2-quinolinil)ethenyl)phenyl)-3-(2-(1-hydroxy-1-methylethyl)phenyl)propyl)thio)methyl)cyclopropane acetic acid benzylamine salt To 10 g of montelukast acid obtained from Example 1, 100 ml of ethyl acetate was introduced. At room temperature, to the resultant product, 1.9 g of benzylamine was introduced, followed by stirring for 24 hours. The produced solid was filtered, washed with 33 ml of ethyl acetate, and vacuum-dried at 40° C. for 12 hours so as to provide 7 g of montelukast amine salt (yield: 59%, purity: 94.5%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm) 8.11(d, 1H), 8.04(d, 1H), 7.61~7.78(m, 4H), 7.09~7.47(m, 14H), 4.02(t, 1H), 3.88 (s, 2H), 3.15~3.22(m, 1H), 2.90~2.97(m, 1H), 2.70(d, 1H), 2.19~2.61(m, 5H), 1.61(d, 6H), 0.45~0.57(m, 4H)

COMPARATIVE EXAMPLE 3

Preparation of 1-(((1(R)-(3-(2-(7-chloro-2-quinolinil)ethenyl)phenyl)-3-(2-(1-hydroxy-1-methylethyl)phenyl)propyl)thio)methyl)cyclopropane acetic acid 4-methoxy benzylamine salt To 10 g of montelukast acid obtained from Example 1, 200 ml of isopropyl alcohol was introduced, followed by stirring. At room temperature, to the resultant product, 2.5 g of 4-methoxy benzylamine was introduced, followed by stirring. When crystallized, the reaction mixture was heated up to 50° C. Then, the reaction mixture was stirred while 100 ml of normal hexane was dropped into it. The resultant product was stirred at 50° C. for 3 hours, gradually cooled to room temperature, further stirred for 3 hours, and filtered.

Through vacuum-drying at 50° C. for 12 hours, 8.6 g of montelukast 4-methoxy benzylamine salt was obtained (yield: 70%, purity: 95.5%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm) 8.06(d, 1H), 8.01(d, 1H), 7.61~7.70(m, 4H), 7.05~7.44(m, 11H), 6.79~6.83(m, 2H), 3.98(t, 1H), 3.82(s, 2H), 3.79(s, 3H), 3.14~3.23(m, 1H), 2.80~2.90(m, 1H), 2.53(dd, 2H), 2.13~2.35(m, 4H), 1.58(d, 6H), 1.43(d, 6H), 0.35~0.53 (m, 4H)

COMPARATIVE EXAMPLE 4

Preparation of 1-(((1(R)-(3-(2-(7-chloro-2-quinolinilethenyl)phenyl)-3-(2-(1-hydroxy-1-methylethyl)phenyl)propyl)thio)methyl)cyclopropane acetic acid dicyclohexylamine salt To 10 g of montelukast acid obtained from Example 1, 100 ml of ethyl acetate was introduced. At room temperature, 3.1 g of dicyclohexylamine was introduced thereto. A seed was introduced, and stirring was carried out for 1 hour. 200 ml of hexane was dropped into it for 2 hours, and left at 20° C. for 24 hours.

The produced crystal was filtered, washed with an ethyl acetate/hexane (1:2) solution, and vacuum-dried at 40° C. for 12 hours so as to provide 10.6 g of montelukast amine salt (yield: 81%, purity: 97.9%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

$^1$H-NMR (300 MHz, CDCl3) δ (ppm) 8.10(d, 1H), 8.07(d, 1H), 7.62~7.72(m, 4H), 7.08~7.50(m, 9), 3.98(t, 1H), 3.13~3.20(m, 1H), 2.13~2.90(m, 9H), 1.94~1.97(m, 4H), 1.73~1.77(m, 4H), 1.59(d, 6H), 1.11~1.43(m 12H), 0.31~0.54(m, 4H)

COMPARATIVE EXAMPLE 5

Preparation of 1-(((1(R)-(3-(2-(7-chloro-2-quinolinilethenyl)phenyl)-3-(2-(1-hydroxy-1-methylethyl)phenyl)propyl)thio)methyl)cyclopropane acetate 10 g of montelukast amine salt obtained from Comparative Example 1 was dissolved in 100 ml of methylene chloride, and 10% acetic acid was dropped into it so as to adjust the pH to a range of 4 to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was dissolved in 20 ml of water and freeze-dried so as to provide 8.5 g of montelukast sodium salt (yield: 99%, purity: 96.7%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

COMPARATIVE EXAMPLE 6

Preparation of sodium 1-(((1(R)-(3-(2-(7-chloro-2-quinolinil)ethenyl)phenyl)-3-(2-(1-hydroxy-1-methylethyl)phenyl)propyl)thio)methyl)cyclopropane acetate 10 g of montelukast amine salt obtained from Comparative Example 2 was dissolved in 100 ml of methylene chloride, and 10% acetic acid was dropped into it so as to adjust the pH to a range of 4 to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was dissolved in 20 ml of water and freeze-dried so as to provide 8.7 g of montelukast sodium salt (yield: 99%, purity: 94.5%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

COMPARATIVE EXAMPLE 7

Preparation of sodium 1-(((1(R)-(3-(2-(7-chloro-2-quinolinil)ethenyl)phenyl)-3-(2-(1-hydroxy-1-methylethyl)phenyl)propyl)thio)methyl)cyclopropane acetate 10 g of montelukast amine salt obtained from Comparative Example 3 was dissolved in 100 ml of methylene chloride, and 10% acetic acid was dropped into it so as to adjust the pH to a range of 4 to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was dissolved in 20 ml of water and freeze-dried so as to provide 8.3 g of montelukast sodium salt (yield: 99%, purity: 95.5%, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

COMPARATIVE EXAMPLE 8

Preparation of sodium 1-(((1(R)-(3-(2-(7-chloro-2-quinolinil)ethenyl)phenyl)-3-(2-(1-hydroxy-1-methylethyl)phenyl)propyl)thio)methyl)cyclopropane acetate 10 g of montelukast amine salt obtained from Comparative Example 4 was dissolved in 100 ml of methylene chloride, and 10% acetic acid was dropped into it so as to adjust the pH to a range of 4 to 4.5. Then, the resultant product was washed with distilled water twice. The organic layer was concentrated and dissolved in 100 ml of methanol. Then, 0.54 g of NaOH dissolved in 1.7 mL of distilled water was introduced, and 1 g of activated carbon was added, followed by stirring for 1 hour and filtration. After vacuum-concentration of the solvent, the resultant product was dissolved in 20 ml of water and freeze-dried so as to provide 7.8 g of montelukast sodium salt. (yield: 99%, purity: 97.9, HPLC wavelength: 238 nm, Phenyl column, 4.6×250 mm, moving phase A: 0.1% TFA in water, B: 0.1% TFA in ACN, flowing at 6:4 to 1:9 for 20 min at a flow rate 1.5 mL/min).

Experimental results of Examples and Comparative Examples are noted in Table 1.

TABLE 1

| | Montelukast acid or salt | yield (%) | purity (%) |
|---|---|---|---|
| Example 1 | Montelukast acid | 95 | 91.6 |
| Example 2 | 4-chlorobenzylamine salt | 87 | 98.5 |
| Example 3 | 4-bromobenzylamine salt | 88 | 98.3 |
| Example 4 | 4-chlorobenzylamine salt | 93 | 99.6 |
| Example 5 | Montelukast sodium salt | 99 | 99.6 |
| Example 6 | Montelukast sodium salt | 98 | 99.7 |
| Comp. Example 1 | α-methyl benzylamine salt | 76 | 96.7 |
| Comp. Example 2 | benzylamine salt | 59 | 94.5 |
| Comp. Example 3 | 4-methoxy benzylamine salt | 70 | 95.5 |
| Comp. Example 4 | dicyclohexyl amine salt | 81 | 97.9 |
| Comp. Example 5 | Montelukast sodium salt | 99 | 96.7 |
| Comp. Example 6 | Montelukast sodium salt | 99 | 94.5 |
| Comp. Example 7 | Montelukast sodium salt | 99 | 95.5 |
| Comp. Example 8 | Montelukast sodium salt | 99 | 97.9 |

As noted in Table 1, for the yield and the purity of an amine salt, 4-halo benzylamine salts in Examples 2 to 4 showed a much higher yield and a much higher purity, compared to those (yield: 59 to 81%, and purity: 94.5% to 97.9%) of other amine salts in Comparative Examples 1 to 4.

Also, in Table 1, montelukast sodium salts from Examples 5 and 6, and Comparative Examples 5 to 8 showed a yield of 90% or more. However, with regard to the yield of an amine salt, the sodium salt prepared from Example 5 showed a yield of 92.07%, and the sodium salt from Example 6 showed a yield of 86.24%. Also, with regard to the yield of an amine salt, the sodium salts from Comparative Examples 5 to 8 showed a yield of 58.41% to 80.19%. Accordingly, it can be determined that the sodium salt according to the present invention showed a significantly high yield. Furthermore, it can be found that montelukast sodium salts prepared from Examples 5 and 6 showed a high purity (99.6% or more), compared to those of Comparative Examples 5 to 8.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A montelukast 4-halobenzylamine salt represented by Formula 2 below:

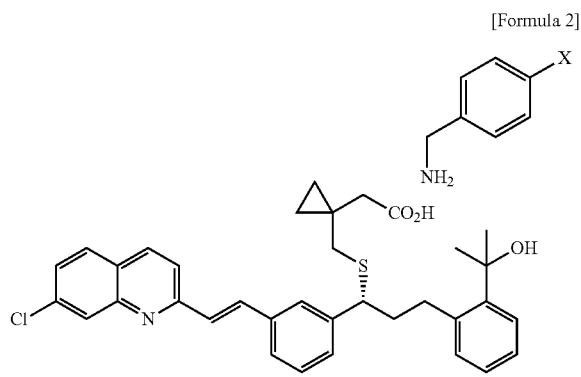

[Formula 2]

wherein in Formula 2, X represents F, Cl, Br or I.

2. A method for preparing a montelukast 4-halobenzylamine salt represented by Formula 2 below, wherein a compound represented by Formula 3 below is reacted with 4-halobenzylamine:

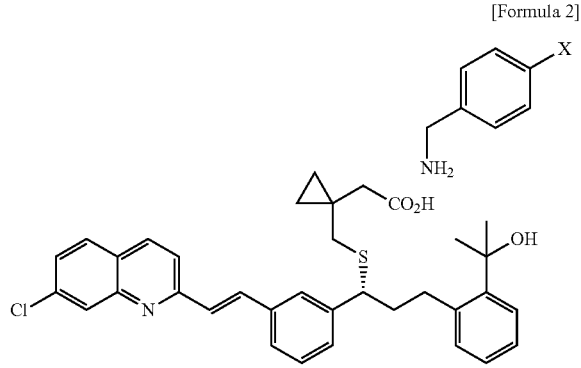

[Formula 2]

-continued

[Formula 3]

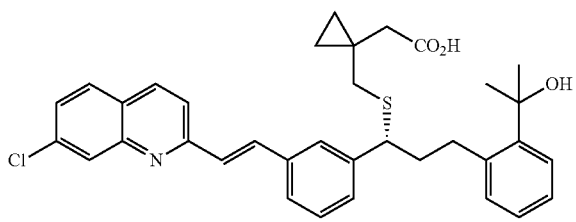

wherein in Formula 2, X represents F, Cl, Br or I.

3. A method for preparing a montelukast 4-halobenzylamine salt represented by Formula 2 below, the method comprising the steps of:
   a) obtaining a compound represented by Formula 3 below by reacting a compound represented by Formula 5 below with methanesulfonyl chloride, then with a compound represented by Formula 4, followed by base treatment; and
   b) obtaining a compound represented by Formula 2 by reacting the obtained compound represented by Formula 3 with 4-halobenzylamine,

[Formula 2]

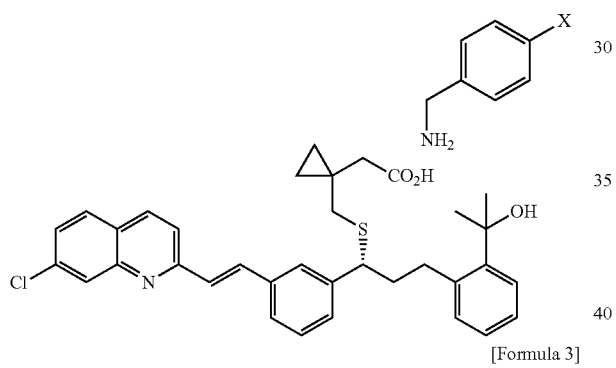

[Formula 3]

[Formula 4]

[Formula 5]

wherein in Formula 2, X represents F, Cl, Br or I.

4. The method as claimed in claim 3, wherein step a) is to obtain the compound represented by Formula 3 by reacting the compound represented by Formula 5 with methanesulfonyl chloride, then with the compound represented by Formula 4, followed by the base treatment, without an additional obtaining process.

5. The method as claimed in claim 3, wherein in step a), the reaction with the compound represented by Formula 4 is carried out in at least one base selected from the group consisting of cesium carbonate, lithium hydroxide, sodium hydroxide, potassium hydroxide, potassium carbonate, and sodium carbonate.

6. The method as claimed in claim 3, wherein in step a), the reaction with the compound represented by Formula 4 is carried out in cesium carbonate.

7. The method as claimed in any one of clams 2 to 6, wherein the step of reacting the compound represented by Formula 3 with the 4-halobenzylamine is carried out in at least one solvent selected from the group consisting of ethanol, isopropyl alcohol, acetone, acetonitrile, ethyl acetate, tetrahydrofuran, methylene chloride, chloroform, toluene, xylene, hexane, cyclohexane and heptane.

8. A method for preparing a montelukast sodium salt represented by Formula 1 below, the method comprising the steps of:
   1) obtaining a compound represented by Formula 2 below by reacting a compound represented by Formula 3 below with 4-halobenzylamine; and
   2) treating the obtained compound represented by Formula 2 with acid, and attaching sodium thereto,

[Formula 1]

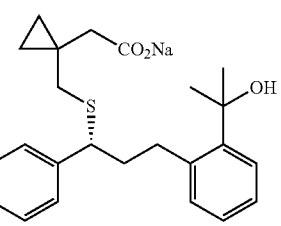

[Formula 2]

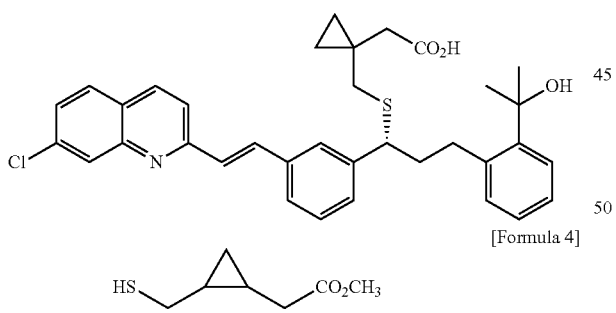

[Formula 3]

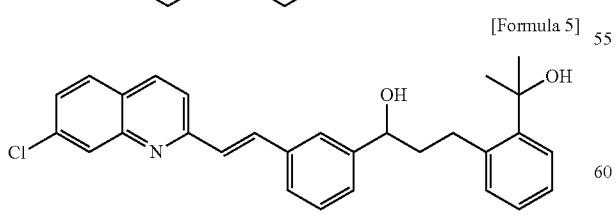

wherein in Formula 2, X represents F, Cl, Br or I.

9. A method for preparing a montelukast sodium salt represented by Formula 1 below, the method comprising the steps of:

a) obtaining a compound represented by Formula 3 below by reacting a compound represented by Formula 5 below with methanesulfonyl chloride, then with a compound represented by Formula 4 below, followed by base treatment;
b) obtaining a compound represented by Formula 2 below by reacting the obtained compound represented by Formula 3 with 4-halobenzylamine; and
c) treating the obtained compound represented by Formula 2 with acid, and attaching sodium thereto,

[Formula 1]

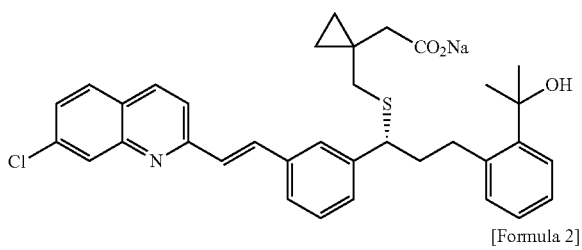

[Formula 2]

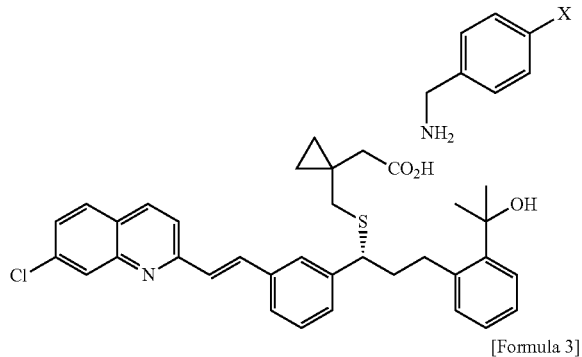

[Formula 3]

[Formula 4]

[Formula 5]

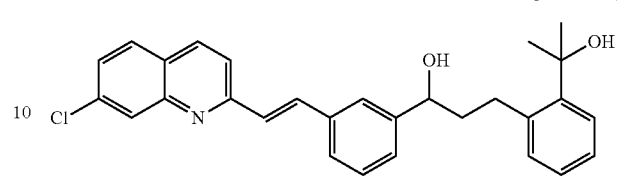

wherein in Formula 2, X represents F, Cl, Br or I.

10. The method as claimed in claim 9, wherein step a) is to obtain the compound represented by Formula 3 by reacting the compound represented by Formula 5 with methanesulfonyl chloride, then with the compound represented by Formula 4, followed by the base treatment, without an additional obtaining process.

11. The method as claimed in claim 9, wherein in step a), the reaction with the compound represented by Formula 4 is carried out in at least one base selected from the group consisting of cesium carbonate, lithium hydroxide, sodium hydroxide, potassium hydroxide, potassium carbonate, and sodium carbonate.

12. The method as claimed in claim 9, wherein in step a), the reaction with the compound represented by Formula 4 is carried out in cesium carbonate.

13. The method as claimed in any one of claimed 8 or 12, wherein the step of obtaining the compound represented by Formula 2 by reacting the compound represented by Formula 3 with the 4-halobenzylamine is carried out in at least one solvent selected from the group consisting of ethanol, isopropyl alcohol, acetone, acetonitrile, ethyl acetate, tetrahydrofuran, methylene chloride, chloroform, toluene, xylene, hexane, cyclohexane and heptane.

14. The method as claimed in any one of claims 8 or 12, wherein in the step of attaching sodium, at least one selected from the group consisting of sodium hydroxide, sodium methoxide, and tert- sodium butoxide is added.

* * * * *